US009227009B2

(12) United States Patent
Lanin et al.

(10) Patent No.: US 9,227,009 B2
(45) Date of Patent: Jan. 5, 2016

(54) PEN-TYPE INJECTOR WITH ERGONOMIC BUTTON ARRANGEMENT

(75) Inventors: Irina Lanin, Frankfurt am Main (DE); Christopher Langley, Warwickshire (GB); Daniel Tyce, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 754 days.

(21) Appl. No.: 13/266,854

(22) PCT Filed: Apr. 29, 2010

(86) PCT No.: PCT/EP2010/055845
§ 371 (c)(1),
(2), (4) Date: Mar. 15, 2012

(87) PCT Pub. No.: WO2010/125154
PCT Pub. Date: Nov. 4, 2010

(65) Prior Publication Data
US 2012/0165747 A1 Jun. 28, 2012

(30) Foreign Application Priority Data

Apr. 30, 2009 (EP) .................................... 09005998

(51) Int. Cl.
*A61M 3/00* (2006.01)
*A61M 5/142* (2006.01)
(Continued)

(52) U.S. Cl.
CPC ....... *A61M 5/14244* (2013.01); *A61M 5/14566* (2013.01); *A61M 5/31546* (2013.01); *A61M 2205/502* (2013.01)

(58) Field of Classification Search
CPC .................... A61M 2205/50; A61M 5/31546; A61M 2205/502
USPC ........................................ 604/67, 189, 890.1
See application file for complete search history.

(56) References Cited

U.S. PATENT DOCUMENTS

| | | | |
|---|---|---|---|
| 2003/0060765 A1* | 3/2003 | Campbell et al. | ............. 604/131 |
| 2004/0054319 A1* | 3/2004 | Langley et al. | ................. 604/67 |

(Continued)

FOREIGN PATENT DOCUMENTS

| | | |
|---|---|---|
| EP | 0124913 A1 | 11/1984 |
| JP | H08287892 A | 11/1996 |

(Continued)

OTHER PUBLICATIONS

Form PCT/IB/326, Notification Concerning Transmittal of International Preliminary Report on Patentability.

*Primary Examiner* — Emily Schmidt
(74) *Attorney, Agent, or Firm* — McDonnell Boehnen Hulbert & Berghoff LLP

(57) ABSTRACT

A hand-held injection device (2) for injection of a medicament from a first medicament cartridge (40), injection device comprising:

a housing (4) being designed to be held in one hand of a user, the longitudinal direction of the housing (4) running between the thumb and the other fingers of the hand of the user, a drive mechanism (42) for selectively dispensing the medicament from the first medicament cartridge (40), a dial dose mechanism (12, 14), a control panel region (8) with at least two operation buttons (12, 14, 16) disposed therein for activating operation functions of the injection device (2), an electronic control unit for controlling the operation of the drive mechanism 42 in response to the dial dose mechanism (12,14) and a display panel (10), in which the required dosage to be dispensed is presented to the user on the display panel (10), wherein between two of the operation buttons (12, 14, 16) a recess is provided in the control panel region (8) and in that in the recess (R) a discrete button (D) for accessing configuration menus of the injection device is discretely located, wherein the recess and the disposition of the two of the operation buttons (12, 14, 16) are designed such that the location of the discrete button in the recess hinders pressing of the discrete button by a finger.

16 Claims, 5 Drawing Sheets

(51) Int. Cl.
*A61M 5/315* (2006.01)
*A61M 5/145* (2006.01)

(56) References Cited

U.S. PATENT DOCUMENTS

| | | |
|---|---|---|
| 2005/0148938 A1 | 7/2005 | Blomquist |
| 2006/0030836 A1 | 2/2006 | Lee et al. |
| 2007/0100283 A1* | 5/2007 | Causey et al. ............... 604/152 |
| 2008/0072896 A1 | 3/2008 | Setzer et al. |
| 2008/0312604 A1 | 12/2008 | Boesen |
| 2010/0331826 A1* | 12/2010 | Field et al. ................ 604/890.1 |
| 2011/0265788 A1* | 11/2011 | Wu ........................... 128/200.23 |

FOREIGN PATENT DOCUMENTS

| | | |
|---|---|---|
| JP | H08299676 A | 11/1996 |
| JP | 2002272839 A | 9/2002 |
| JP | 2004516110 A | 6/2004 |
| JP | 2007531591 A | 11/2007 |
| JP | 2008000674 A | 1/2008 |
| WO | 02051479 A1 | 7/2002 |
| WO | 02058767 A1 | 8/2002 |
| WO | 2005097237 A1 | 10/2005 |
| WO | 2008067314 A2 | 6/2008 |
| WO | 2008070054 A2 | 6/2008 |
| WO | 2008116109 A1 | 9/2008 |

* cited by examiner

PEN-TYPE INJECTOR WITH ERGONOMIC BUTTON ARRANGEMENT

CROSS REFERENCE TO RELATED APPLICATIONS

The present application is a 35 U.S.C. 371 National Application of PCT/EP2010/055845 filed Apr. 29, 2010 and claims priority to European Patent Application No. 09005998.1, filed Apr. 30, 2009, the entire contents of which are incorporated entirely herein by reference.

The present invention relates to improvements in an injection device, and in particular to improvements regarding the operation button arrangement.

Typically such injection devices are used by those suffering from diabetes to administer a dose of insulin or insulin-type medicine to themselves.

While such pen-type injectors are a considerable improvement upon disposable hypodermic syringes, problems nevertheless remain. It is an advantage of the present invention that it eliminates, or at least substantially reduces such problems. The present invention also provides for improved ease of use and improved interaction with a user.

WO 02/058767 and US 2005/0148938 A1 disclose a hand-held injection device for injection of a medicament from a medicament cartridge comprising a housing, a dial dose mechanism and a first dose button for incrementing the dosage level and a second dose button for decrementing the dosage level.

An object of the invention is to provide a hand-held injection device including an electronic control unit for controlling the operation of the drive mechanism and a display panel which is comfortable to a user and safe with regard to the operational functions provided to the user.

This object is solved by the features of claim 1. Further examples of the invention are described in the subclaims.

According to the invention a hand-held injection device for injection of a medicament from a first medicament cartridge is provided, the injection device comprising:
  a housing being designed to be held in one hand of a user, the longitudinal direction of the housing running between the thumb and the other fingers of the hand of the user,
  a drive mechanism for selectively dispensing the medicament from the first medicament cartridge,
  a dial dose mechanism by which a user may determine a required dose of medicament to be dispensed, comprising two dose dialing buttons, wherein a first dose button can increment the dosage level and a second dose button 14 can decrement the dosage level,
  an electronic control unit for controlling the operation of the drive mechanism in response to the dial dose mechanism and
  a display panel, in which the required dosage to be dispensed is presented to the user on the display panel.

According to the invention, between two of the operation buttons a recess is provided in the control panel region and in that in the recess a discrete button for accessing configuration menus of the injection device is discretely located, wherein the recess and the disposition of the two of the operation buttons are designed such that the location of the discrete button in the recess hinders pressing of the discrete button by a finger, particularly, especially when one of the operation buttons is intended to be pressed by a finger of a user.

According to an example of the invention, the discrete button and the recess are designed such that the upper side of the discrete button lies at least 1 mm under the region of the surface of the housing which surrounds the recess.

In this regard, the injection device can comprise two dose dialing buttons, wherein a first dose button can increment the dosage level and a second dose button can decrement the dosage level, and in that the recess with the discrete button is located between the two dose dialing buttons lying adjacent to each other.

According to the invention the first dose button and the second dose button are disposed on one side of the housing and such that the connection line of the first dose button and the second dose button is running across the longitudinal direction of the housing.

In this context, the expression "across" means that the connection line between the first dose button and the second dose button forms an angle with the longitudinal direction of the housing between 45 degrees and 135 degrees.

One advantage of the invention is that the dose dialing buttons are arranged in a convenient group so that the device can be held in one hand and the buttons pressed with the thumb of the same hand. Alternatively the device may be held comfortably and securely in one hand with the buttons place for conveniently for access with a finger from the other hand.

When the user holds the injection device in one hand and tries to press the first dose button and a second dose button order to adjust a dose of medicament to be dispensed, the movability of the thumb is limited by the dimension of the housing. Therefore, the arrangement of the first dose button and a second dose button according to the state of the art is not ergonomically designed as it requires some effort to the user to first press one of the dose buttons, then move the thumb tip from the first dose button to the second dose button and then press the second dose button. With the solution according to the invention, it is easier to the user to move the thumb tip between the first and the second dose button and press the one or the other dose button. It should be considered that users of an injection device for a medicament could have limited ability to coordinate the movement of the fingers. There are also users who might not have the second hand available for selecting a button of the injection device when holding the same in a first hand. A hand-held injection device having the features of the invention and particularly when designed as electro-mechanical injection device requires a more simple movement of the thumb of the user in order to press the first dose button and then press the second dose button or in order to move the thumb tip between the two dose buttons.

According to the invention, the first dose button and the second dose button are disposed on one side of the housing and such that the connection line of the first dose button and the second dose button is running vertically to the longitudinal direction of the housing.

According to an example of the invention, the housing is designed symmetrically to the longitudinal direction.

According to another example of the invention, the first dose button and the second dose button are disposed in a control panel region of the housing and in that the control panel region includes an arm button to make the dose button active.

The electronic control unit can be designed such that the arm button has to be held down for a predetermined period of time before the injection device becomes armed.

An advantage an example of the invention having a arm button is that with the arrangement of the first dose button and a second dose button on one side of the housing for a user having restricted movability of his thumb the probability of an erroneously selection of the arm button is avoided. For the user, the injection device is more comfortable for use.

At the first end of the main housing of the injection device there is also provided a dispense button. The dispense button is located and sized to minimize the likelihood of accidental operation by the user while operating other functions. Additionally or alternatively, a primer button is also provided on the second end of the housing.

In a further example of the invention, the injection device can be designed such that when the required dose of medicament is not dispensed within a predetermined time period the electronic control unit resets to allow the user subsequently to operate the dial dose mechanism to dial a new required dose.

In a further example of the invention, the injection device can be designed such that within the predetermined time period the user may reset the electronic control unit to allow the user to operate the dial dose mechanism to dial the new required dose.

In a further example of the invention, the injection device can be designed such that the electronic control unit records a history of the dispensing of doses of medicament.

The invention will now be described, by way of example only, with reference to the accompanying drawings, in which.

Figure 1A:
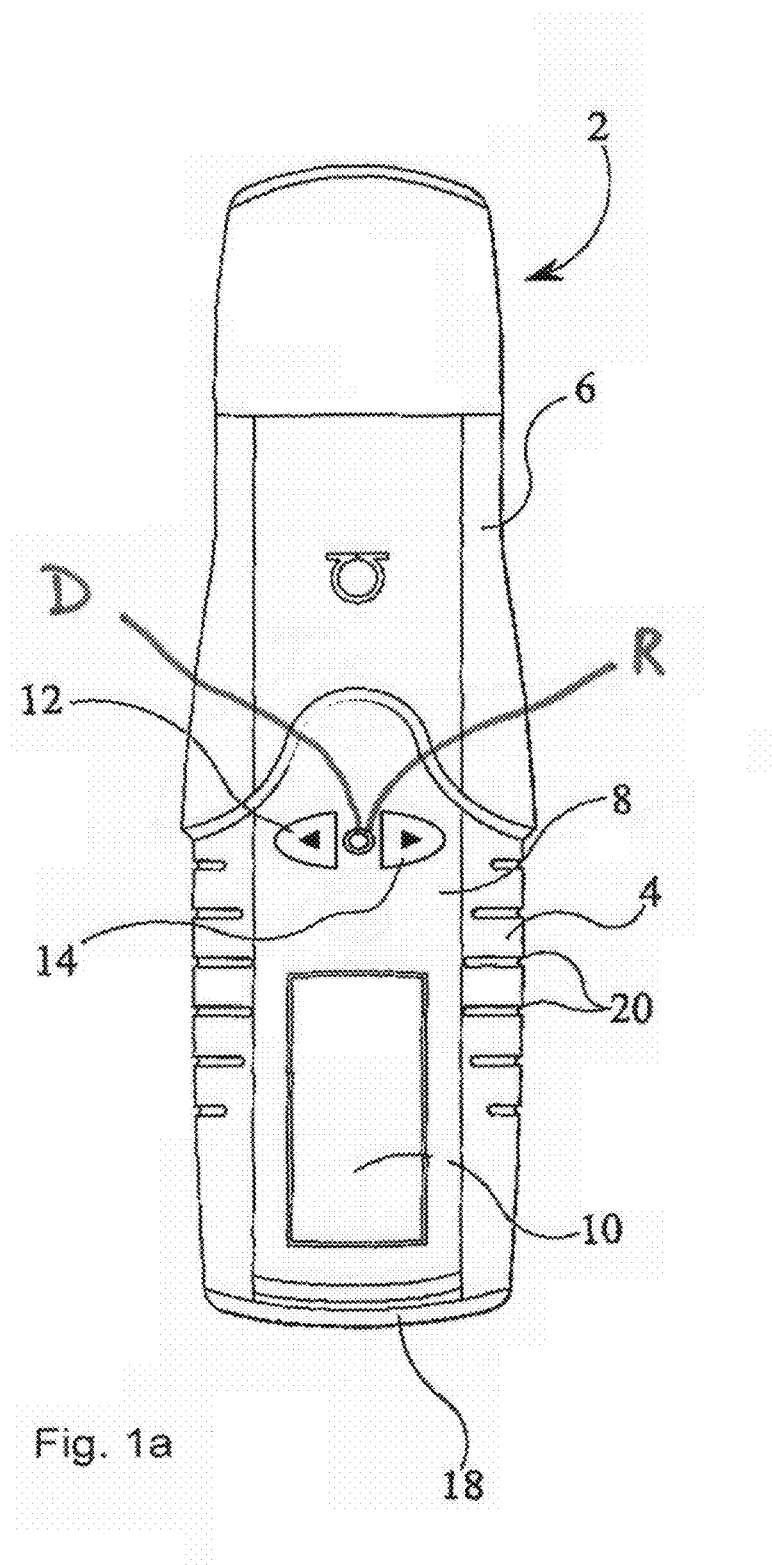
FIG. 1a shows a plan view of a pen-type injector in accordance with the present invention.
Figure 1B:
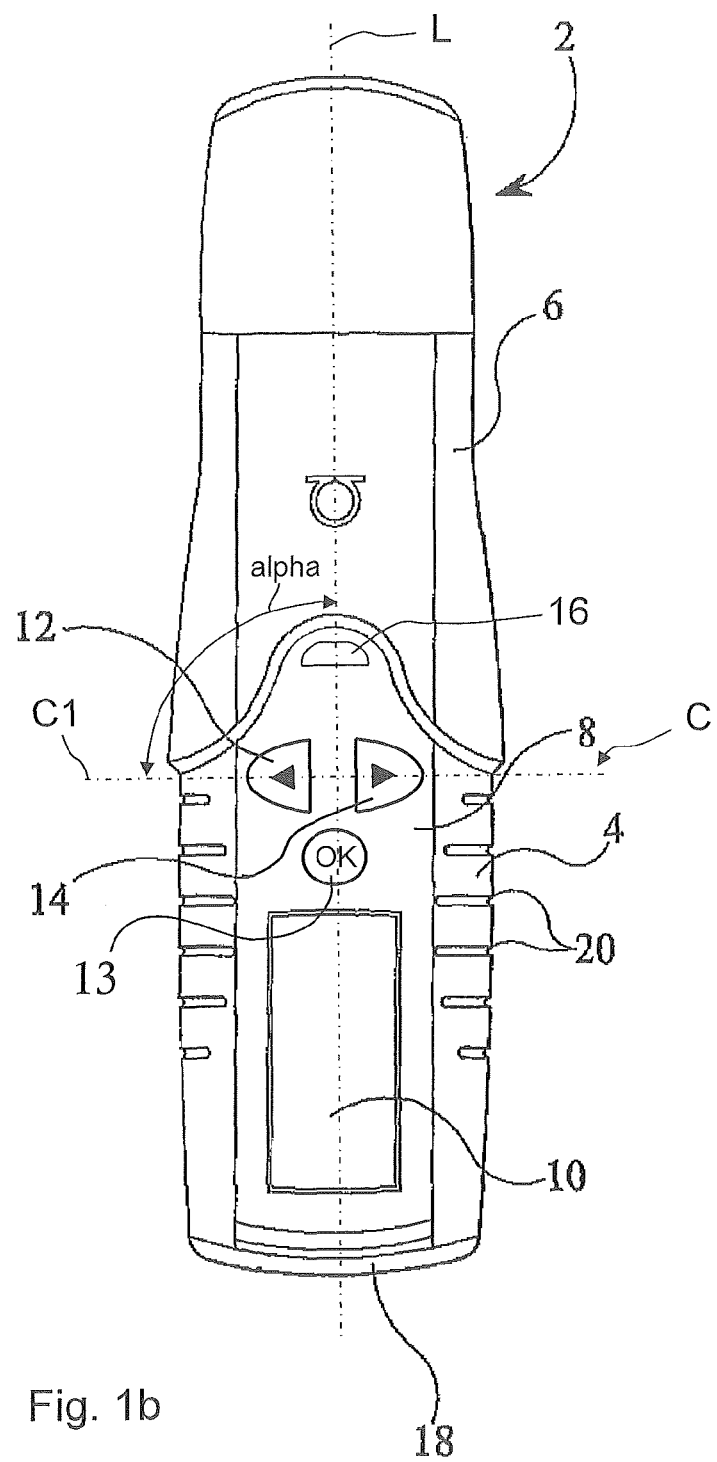
FIG. 1b shows a plan view of a pen-type injector in accordance with the present invention highlighting geometrical features.
Figure 2:
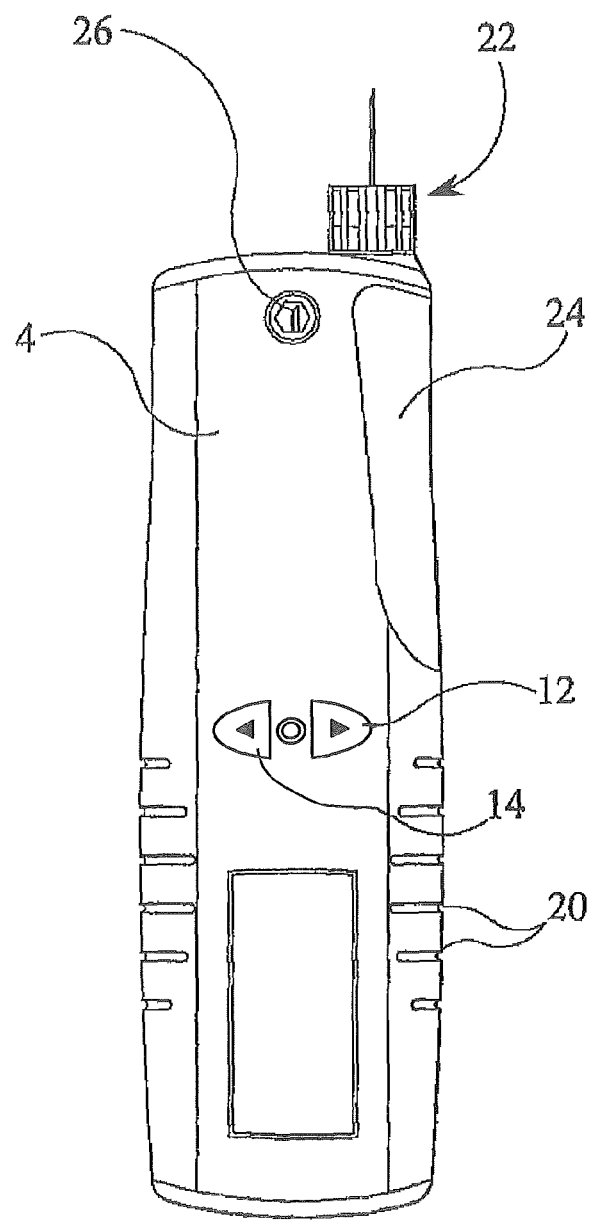
FIG. 2 shows a similar view to FIG. 1 with an end cap of the injector omitted.
Figure 3:
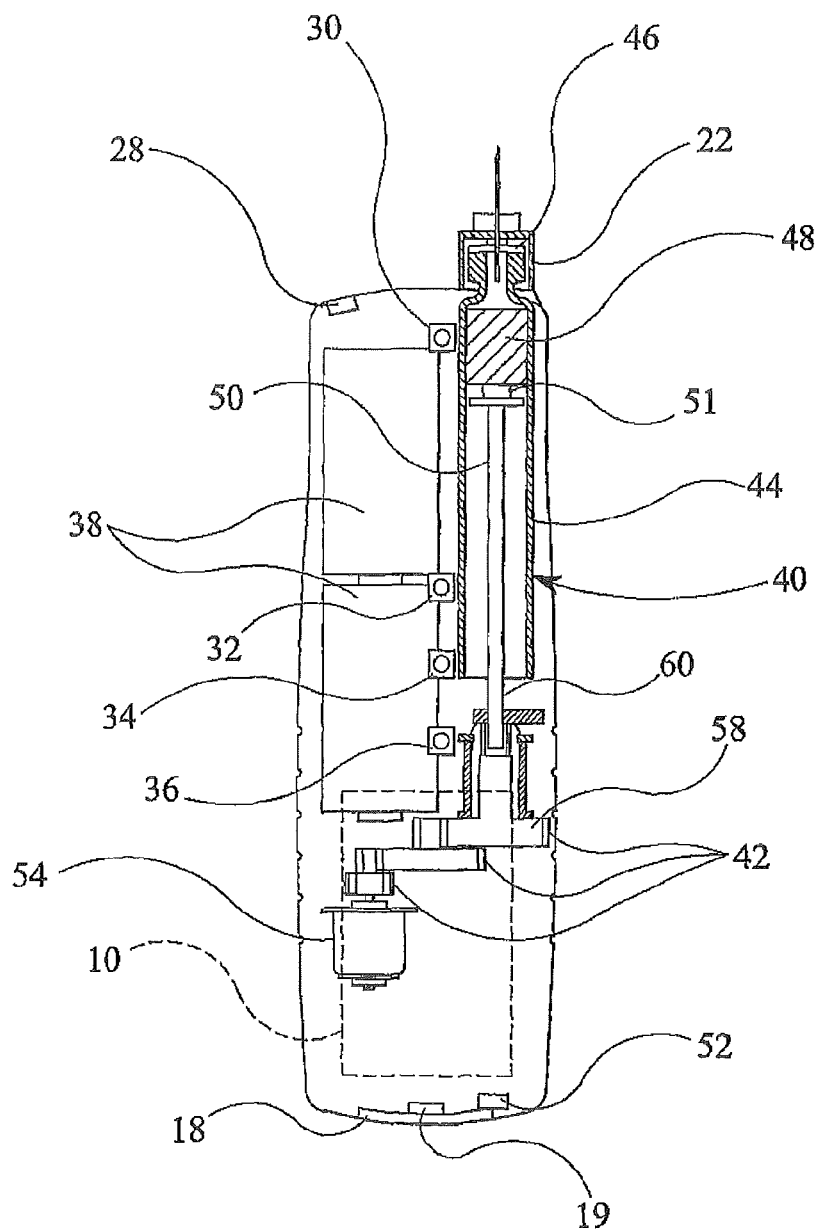
FIG. 3 shows a cross-sectional view of the injector of FIGS. 1 and 2.
Figure 4:
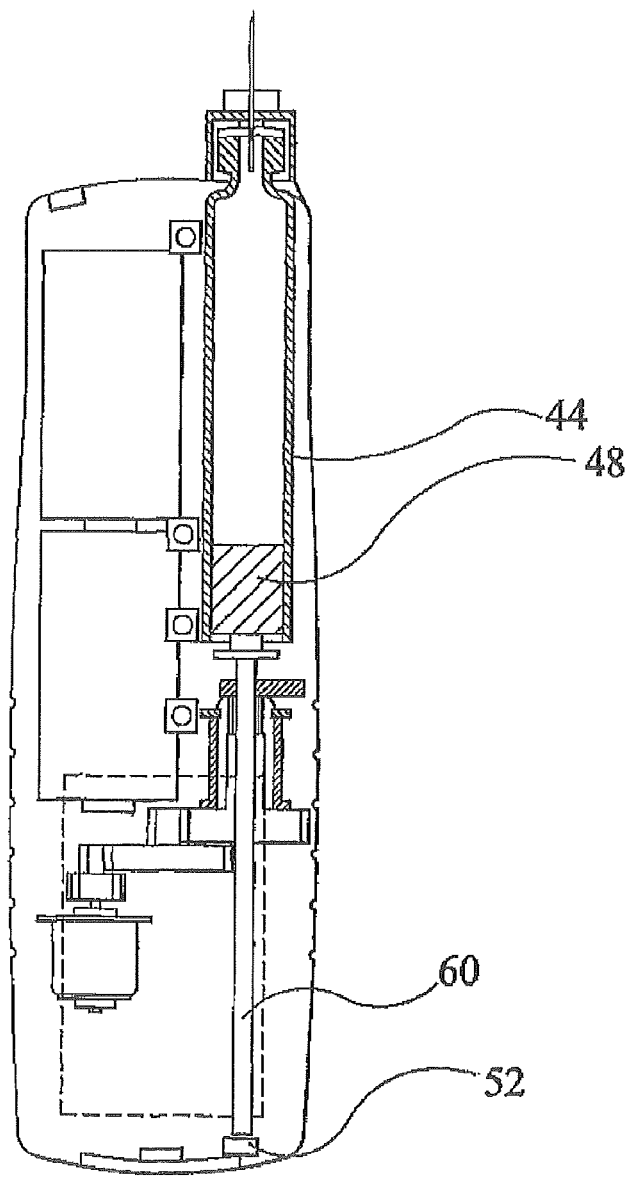
FIG. 4 shows a cross-sectional view of the injector of FIGS. 1-3.

Referring first to FIGS. 1 to 3, there can be seen a pen-type injector 2 in accordance with the present invention. The injector 2 comprises a main housing 4 to which is releasably secured an end cap or cover 6.

Referring to FIG. 1a, at a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 8 in the illustrated embodiment also includes an arm button. In the control panel region 8 also an ok-button or confirmation button can be located by which an input for example of the first dose button 12 and/or the second dose button 14 can be confirmed.

According to an example of the invention, the control panel region 8 is located within 30% and 70% of the complete length for the device 2 in its longitudinal direction. This means that particularly the first dose button 12, the second dose button 14, the arm button and optionally the ok-button or confirmation button lie within this area.

At the first end of the main housing there is also provided a dispense button 18.

Preferably, when not depressed, the dispense button 18 is flush with the main housing 4.

According to the invention, between two of the dose buttons 12, 14 and the arm button a recess R is provided in the control panel region 8 and in that in the recess R a discrete button D which is particularly provided for accessing configuration menus of the injection device is discretely located, wherein the recess and the disposition of the two of the dose buttons 12, 14 and the arm button are designed such that the location of the discrete button in the recess hinders pressing of the discrete button by a finger, particularly when one of the dose buttons 12, 14 and the arm button is intended to be pressed. The discrete button D is located such in the recess R that when the discrete button D is in its initial or non-operated state, its upper side is sunk-in the region of the surface of the housing 4 which surrounds the recess R. In particular, the discrete button D and the recess R can be designed such that the upper side of the discrete button D lies at least 1 mm under the region of the surface of the housing 4 which surrounds the recess R. In a further example of the invention, the discrete button D has a diameter of maximal 5 mm.

Thereby, the discrete button D is positioned such that it can be pressed and moved downward and put into an activation state for activating the configuration menu only by inserting the tip of a tapered object like a pen. This means that the sunk-in disposition of the discrete button D provides a safety function.

Along a longitudinal axis of the injector 2, on each side of the control panel region 8 of the housing 4 a number of grooves or recesses 20 are provided. These aid the gripping of the injector 2 by a user. In another example of the invention no such grooves or recesses 20 are provided on the housing. The housing 4 can also be designed such that it adapts to the form of the inner side of the hand so that the housing lies safe in the hand of a user during operation. In an example of the invention, the longitudinal direction runs through the points on the surface of the housing 4 which are lying farthest apart from each other.

Generally, the longitudinal axis of the housing 4 is defined such that, when the hand-held injection device is lying in the hand of a user, the longitudinal axis is running between the thumb and the other fingers of the hand of the user.

In an example of the invention, the hand-held injection device 2 can comprise a needle to injection of a required dose of the medicament and the longitudinal direction of the housing 4 is running along the longitudinal direction of the needle. Particularly the longitudinal direction of the housing 4 is running parallel the longitudinal direction of the needle.

In a further embodiment, the housing is of symmetrical form and the longitudinal axis is the symmetry axis of the housing.

According to the invention, the connection line of the first dose button with the second dose button is running across the longitudinal direction of the housing. Particularly, by crossing of the connection line of the first dose button 12 with the second dose button 14 with the longitudinal direction an angle alpha (FIG. 1) is formed between one section of the said connection line lying on one side of the longitudinal direction and the longitudinal direction of the housing 4 which angle is lying between 45 degrees and 135 degrees. In the embodiment of FIG. 1 the angle alpha amounts to 90 degrees.

According to an example of the invention, the connection line runs through the center of area of the first dose button 12 and the second dose button 14.

According to an example of the invention the arm button is located above or below the connection line of the first dose button 12 and the second dose button 14. Particularly, the arm button is located on the longitudinal axis of the housing 4. Thereby, the likelihood that a user presses the arm button erroneously while operating the first dose button 12 and the second dose button 14 in alternation, is considerably diminished.

Referring to FIG. 1b, at a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 8 in the illustrated embodiment also includes an arm button 16. In the control panel region 8 also an ok-button or confirmation button 13 can be located by which an input for example of the first dose button 12 and/or the second dose button 14 can be confirmed.

According to an example of the invention, the control panel region 8 is located within 30% and 70% of the complete length for the device 2 in its longitudinal direction L. This means that particularly the first dose button 12, the second dose button 14, the arm button 16 and optionally the ok-button or confirmation button 13 lie within this area.

At the first end of the main housing there is also provided a dispense button 18.

Preferably, when not depressed, the dispense button 18 is flush with the main housing 4.

According to the invention, between two of the operation buttons 12, 14, 16 a recess R is provided in the control panel region 8 and in that in the recess R a discrete button D which is particularly provided for accessing configuration menus of the injection device is discretely located, wherein the recess and the disposition of the two of the operation buttons 12, 14, 16 are designed such that the location of the discrete button in the recess hinders pressing of the discrete button by a finger, particularly when one of the operation buttons 12, 14, 16 is intended to be pressed. The discrete button D is located such in the recess R that when the discrete button D is in its initial or non-operated state, its upper side is sunk-in the region of the surface of the housing 4 which surrounds the recess R. In particular, the discrete button D and the recess R can be designed such that the upper side of the discrete button D lies at least 1 mm under the region of the surface of the housing 4 which surrounds the recess R. In a further example of the invention, the discrete button D has a diameter of maximal 5 mm.

Thereby, the discrete button D is positioned such that it can be pressed and moved downward and put into an activation state for activating the configuration menu only by inserting the tip of a tapered object like a pen. This means that the sunk-in disposition of the discrete button D provides a safety function.

Along a longitudinal axis L of the injector 2, on each side of the control panel region 8 of the housing 4 a number of grooves or recesses 20 are provided. These aid the gripping of the injector 2 by a user. In another example of the invention no such grooves or recesses 20 are provided on the housing. The housing 4 can also be designed such that it adapts to the form of the inner side of the hand so that the housing lies safe in the hand of a user during operation. In an example of the invention, the longitudinal direction runs through the points on the surface of the housing 4 which are lying farthest apart from each other.

Generally, the longitudinal axis L of the housing 4 is defined such that, when the hand-held injection device is lying in the hand of a user, the longitudinal axis L is running between the thumb and the other fingers of the hand of the user.

In an example of the invention, the hand-held injection device 2 can comprise a needle to injection of a required dose of the medicament and the longitudinal direction of the housing 4 is running along the longitudinal direction L of the needle. Particularly the longitudinal direction L of the housing 4 is running parallel the longitudinal direction L of the needle.

In a further embodiment, the housing is of symmetrical form and the longitudinal axis L is the symmetry axis of the housing.

According to the invention, the connection line of the first dose button with the second dose button is running across the longitudinal direction of the housing. Particularly, by crossing of the connection line C of the first dose button 12 with the second dose button 14 with the longitudinal direction L an angle alpha (FIG. 1) is formed between one section C1 of the said connection line C lying on one side of the longitudinal direction L and the longitudinal direction L of the housing 4 which angle is lying between 45 degrees and 135 degrees. In the embodiment of FIG. 1 the angle alpha amounts to 90 degrees.

According to an example of the invention, the connection line C runs through the center of area of the first dose button 12 and the second dose button 14.

According to an example of the invention the arm button 16 is located above or below the connection line of the first dose button 12 and the second dose button 14. Particularly, the arm button 16 is located on the longitudinal axis L of the housing 4. Thereby, the likelihood that a user presses the arm button 16 erroneously while operating the first dose button 12 and the second dose button 14 in alternation, is considerably diminished.

Referring to FIGS. 2 and 3, at a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A primer button 26 is also provided on the second end of the housing 4. It will be understood that when the end cap 6 is in place over the second end of the housing, it will not be possible inadvertently to depress the primer button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown. With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper.

When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position.

Tripping of the switch end stop 52 may release a catch or other fastening device to allow access to the main housing 4 for replacement of the cartridge 40.

The drive mechanism 42 is operated by a motor 54 under the control of an electronic control unit (not shown). The motor 54 should be reversible in order to allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

The functionality of a pen-type injector in accordance with the present invention will now be described, in particular with reference to FIGS. 1, 2, 3 and 4.

The injector 2 is provided with an electronic control unit. The electronic control unit is coupled both to the drive mechanism and a user interface. The user interface includes the display panel 10 as well as the user operable buttons (and associated contacts).

The electronic control unit is microprocessor based. Either volatile or non-volatile memory may be used for storage of "dose history" and patient specific information.

The electronic control unit is preferably powered from the injector power source 38.

The injector 2 preferably also includes a port for communication between the electronic control unit and an external apparatus such as a personal computer.

The injector 2 also has a priming detection facility (such as a tilt switch or accelerometer) to identify when the injector 2 is inverted. On detection of an inverted position (needle up) the injector 2 will automatically change state to be ready for priming.

Priming may be initiated by depression of the primer button 26 to cause a fixed small dispense action. The electronic control unit may cause a speaker to sound when the primer button 26 is depressed.

The primer button 26 is inactive at all other times. When the primer button 26 is active, all other buttons in the control panel region are inactive, that is those buttons which are to be used to set or dispense a dose.

The electronic control unit may cause a speaker to sound when the arm button 16 is depressed for a sufficient period of time to provide audible feedback for the user.

The function of the arm button 16 is to make the dose button 18 active. The arm button is preferably held down for a predetermined period of time before the injector 2 becomes armed. The armed status may additionally be shown on the display panel 10.

The functionality of the arm button is preferably linked to the cover detection switch 28 such that the arm button 16 will only function to arm the injector 2 when the cover 6 is not present.

Additionally, in a preferred embodiment, a clock within the electronic control unit will detect whether the dose button 18 has been pressed within a specified time interval following arming of the injector 2. If the dose button 18 has not been depressed within the specified time interval the electronic control unit will disarm the injector 2.

Alternatively, if the arm button is depressed a second time within a predetermined time period by the user, the injector will be disabled.

In an alternative embodiment, the dose button 18 may function as both a prime button and the dose button. When the priming detector is actuated, by the injector 2 being oriented needle up, the dose button 18 would change function to that of the prime button of the previous embodiment.

The buttons of the injector 2 are preferably tactile in nature to provide sensory feedback to the user.

The display panel 10 is typically a LCD display and will provide alphanumeric and graphical information relating to the operation of the device. The display panel 10 preferably indicates the selected dose quantity, the previous dose quantity and the time elapsed since the previous dose was administered. Typically, the time elapsed since the previous dose is limited to a time period within the preceding 48 hours, though other time periods are possible, too.

Additional information which may be displayed includes:
that the injector is armed and ready to dispense (graphical),
that the injector is dispensing (graphical),
that the injector has dispensed the selected dose,
that a user should wait before removing the needle from his body
that this waiting period has elapsed,
the dose history, typically for the last 48 hours, in terms of the dosage taken and the elapsed time between doses,
the quantity of medicament remaining in the cartridge, preferably in terms of dosage units of the medicament,
that the device is in the priming position (either in addition to or instead of the acoustic indication noted above),
the speaker volume setting, for example high, low or muted,
that the injector is nearing the end of its life (for example a battery power level indication-graphical or countdown in terms of the number of days or complete operating cycles to a predetermined expiry of the product life-alphanumeric),
that the needle is probably blocked—that replacement of the cartridge 40 is in progress,
that the dose selected is the maximum available in the cartridge 40—that the maximum dose available is less than the dose expected.

The display panel 10 may offer a user a choice of language options as appropriate for the market and/or user. The text displayed may include that noted above and/or further information. The language option may be pre-programmed or selectable by a user. The user may preferably select the language option by means of a menu provided on the display panel 10.

The currently selected dose value, the previously used dose value and the time (in hours) since the previous dose was dispensed, may all be shown clearly at the same time, in large, easy-to-read characters on the display. Preferably, the display is also provided with a backlight.

The display 10 preferably provides a graphical indication that the selected dose is being dispensed. This may be achieved, for example, as either an animated graphic or a countdown (or a combination of both).

The control buttons have a number of functions. The dose buttons 12, 14 allow a user to select a desired dosage. The arm button 16 allows a user to confirm selection of a desired dosage. The first dose button can increment the dosage level and the second dose button can decrement the dosage level. The dose dialling buttons 12, 14 may be pressed down (and held for a short time, 1-2 seconds) to re-set a dose value to zero. The user can then dial up (or down) in single (or half) increments.

The dose dialling buttons 12, 14 are intended to be pressed once for a single (or half) increment in the selected dose value. In an alternative embodiment, pressing and holding one of the buttons will cause the dose value to start to scroll (up or down) in order to change the dose size more rapidly.

The dispense button 18 allows a user to initiate dispensing of the dosage. The primer button 26 dispenses a unit of dosage from the cartridge 40. Thus, if any air is trapped in the injector 2 this can be expelled by use of the primer button 26. A door release catch is provided to allow access to the cartridge 40.

By pressing the discrete button D a configuration menu of the injection device or the only configuration menu of the injection device is activated and a configuration menu mask is displayed on the display panel 10. The configuration mask provides options which are not provided for the daily use and are particularly not relevant for the dose selection and injection. The configuration mask can provide one or more of the following menu options:

the specified time interval following arming of the injector 2 within which the clock within the electronic control unit will detect whether the dose button 18 has been pressed within a specified time interval, reset of the controller of the control unit of the device 2, general adjustments of the device 2, like adjustment of the date, the clock and/or the alarm.

In another example of the invention, the pressing of the discrete button D can directly cause the reset of the controller of the of the control unit of the device 2.

The disposition between two operation buttons means that the discrete button D is both arranged in a safety arrangement and is visually as well as by haptics always present and consciously available to the user.

Since the cartridge 40 is of a standard size, each cartridge 40 will be emptied by an identical travel of the plunger driven by the drive mechanism. Once the plunger 50 is in the fully extended position, the cartridge 40 is known to be empty and an indication of this will be provided to the user.

When the door release catch is operated for the emptied cartridge 40 to be removed the drive mechanism 42 is operated to reverse a lead screw 60 to withdraw the plunger 50 until the lead screw 60 strikes the end stop switch 52 which is provided at a known reference point.

When a new cartridge 40 is detected, for example by way of a contact switch (not shown), and the door release catch closed, the electronic control unit advances the lead screw 60 until the plunger 50 strikes the cartridge bung 48. This may conveniently be done by fitting a micro-switch 51, such as a dome contact switch to a free end of the plunger 50. Since the exact position of the bung 48 can be calculated with reference to the rear end stop 52, a number of units of medicament stored within the cartridge 40 can be determined. Thus a half empty or incorrectly filled cartridge 40 may be used with the injector 2 of the present invention. The electronic control unit having determined the number of units stored within the cartridge preferably will not allow a dosage larger than that remaining to be dialled up for dispense.

The drive mechanism 42 preferably operates at a constant speed during dispense.

However, at the start of each new cartridge 40 a slower speed may be appropriate to increase the force available to overcome the stiction of the bung 48 in the cartridge 40.

Alternatively, the speed of dispense may be controlled to suit the comfort of the user.

In addition, the drive mechanism may be able to operate at a variable speed. In such a case, the injector 2 will be adapted to detect resistance to dispensing, for example if the medicament, i.e. insulin, is cold it may become more viscous and so provide greater resistance to dispense. The drive mechanism can then slow to deliver more output force and then stop if this has no effect upon the effective dispense action. In other words if, for example, the resistance to dispensing is due a mechanical problem in the injector then the electronic control unit will switch off the drive mechanism, and thus not dispense, rather than seek to dispense further medicament.

Due to the use of an electromechanical drive, the dispense action is initiated by the user operating a switch. This means that the force required to operate the dispense button can be optimized for the comfort and ergonomic requirement of users.

The drive mechanism 42 may additionally comprise a 1 bit encoder (for example an inductive transducer mounted at a first stage in the gear train 56) to detect slipping of the motor. Thus, should the drive mechanism 42 become jammed, this can be detected, the electronic control unit can halt the drive mechanism 42 and indicate to the user that an error has occurred.

The invention claimed is:

1. A hand-held injection device for injection of a medicament from a first medicament cartridge, injection device comprising:

a housing being designed to be held in one hand of a user, a drive mechanism for selectively dispensing the medicament from the first medicament cartridge, a dial dose mechanism comprising a control panel region with at least two operation buttons disposed therein for activating operation functions of the injection device, wherein the injection device is configured to control the operation of the drive mechanism in response to the dial dose mechanism and a display panel, in which the required dosage to be dispensed is presented to the user on the display panel, characterized in that between two of the operation buttons a recess is provided in the control panel region and in that in the recess (R) a discrete button (D) for accessing configuration menus of the injection device is discretely located, wherein the recess and the disposition of the two of the operation buttons are designed such that the location of the discrete button in the recess prevents pressing of the discrete button by a finger, wherein an upper side of the discrete button (D) lies at least 1 mm under a region of the surface of the housing which surrounds the recess (R), and wherein the discrete button (D) has a diameter less than 5 mm.

2. An injection device according to claim 1, characterized in that by pressing the discrete button (D) a configuration menu of the injection device is activated and the configuration menu is displayed on the display panel, wherein the configuration menu provides one or more of the following menu options:

the specified time interval following arming of the injector within which a clock of the injection device will detect whether the dose button has been pressed within a specified time interval, reset of the controller of the control unit of the device, general adjustments of the device, like adjustment of the date, the clock and/or the alarm.

3. An injection device according to claim 1, characterized in that by pressing the discrete button (D) a reset of the injection device is performed.

4. An injection device according to claim 1, characterized in that the injection device comprises two dose dialing buttons, wherein a first dose button can increment the dosage level and a second dose button can decrement the dosage level, and in that the recess (R) with the discrete button (D) is located between the two dose dialing buttons lying adjacent to each other.

5. An injection device according to claim 4, characterized in that the first dose button and the second dose button are disposed on one side of the housing and such that the connection line of the first dose button and the second dose button is running across the longitudinal direction of the housing.

6. An injection device according to claim 4, characterized in that the first dose button and the second dose button are disposed in a control panel region of the housing and in that the control panel region includes an arm button to make the dose button active.

7. An injection device according to claim 6, characterized in that the injection device is configured such that the arm button has to be held down for a predetermined period of time before the injection device becomes armed.

8. An injection device according to claim 6, characterized in that the arm button is located above or below the connection line of the first dose button and the second dose button.

9. An injection device according to claim 8, characterized in that arm button is located on the longitudinal axis (L) of the housing.

10. An injection device according to claim 1, characterized in that the first dose button and the second dose button are disposed on one side of the housing and such that the connection line of the first dose button and the second dose button is running vertically to the longitudinal direction of the housing.

11. An injection device according to claim 1, characterized in that the housing is designed symmetrically to the longitudinal direction.

12. An injection device according to claim 1, characterized in that at the first end of the main housing there is also provided a dispense button.

13. An injection device according to claim 1, characterized in that a primer button is also provided on the second end of the housing.

14. An injection device according to claim 1, characterized in that when the required dose of medicament is not dispensed within a predetermined time period the injection device resets to allow the user subsequently to operate the dial dose mechanism to dial a new required dose.

15. An injection device according to claim 14, characterized in that within the predetermined time period the user may reset the injection device to allow the user to operate the dial dose mechanism to dial the new required dose.

16. An injection device according to claim 1, characterized in that the injection device records a history of the dispensing of doses of medicament.

* * * * *